United States Patent
Behbehani et al.

(10) Patent No.: US 7,801,593 B2
(45) Date of Patent: *Sep. 21, 2010

(54) SYSTEM, SOFTWARE, AND METHOD FOR DETECTION OF SLEEP-DISORDERED BREATHING USING AN ELECTROCARDIOGRAM

(75) Inventors: Khosrow Behbehani, Arlington, TX (US); Sridhar Vijendra, Canton, MI (US); John R. Burk, 440 Horseshoe Trail, Aledo, TX (US) 76008; Edgar A. Lucas, 6605 Cliffside Ct., Fort Worth, TX (US) 76134

(73) Assignees: Board of Regents, The University of Texas System, Austin, TX (US); John R. Burk, Aledo, TX (US); Edgar A. Lucas, Fort Worth, TX (US)

( * ) Notice: Subject to any disclaimer, the term of this patent is extended or adjusted under 35 U.S.C. 154(b) by 63 days.

This patent is subject to a terminal disclaimer.

(21) Appl. No.: 12/030,789

(22) Filed: Feb. 13, 2008

(65) Prior Publication Data

US 2008/0319326 A1 Dec. 25, 2008

Related U.S. Application Data

(63) Continuation of application No. 10/924,227, filed on Aug. 23, 2004, now Pat. No. 7,343,198.

(51) Int. Cl.
*A61B 5/04* (2006.01)
(52) U.S. Cl. ................ 600/509; 600/483; 600/484; 600/515

(58) Field of Classification Search ......... 600/508–513, 600/517, 523; 128/725, 702, 670, 700, 703, 128/706; 364/413.03, 413.06
See application file for complete search history.

(56) References Cited

U.S. PATENT DOCUMENTS 5,092,341 A * 3/1992 Kelen .................. 600/515

(Continued)

OTHER PUBLICATIONS

Al-Abed, et al., A New Method to Detect Obstructive Sleep Apnea Using Fuzzy Classification of Time-Frequency Plots of the Heart Rate Variability, Conference Proceedings, 28th Annual International Conference of IEEE-EMBS, Volume Supplement, Aug. 30, 2006-Sep. 2006, pp. 6493-6496.

(Continued)

*Primary Examiner*—Carl H Layno
*Assistant Examiner*—Paula J Stice
(74) *Attorney, Agent, or Firm*—Fulbright & Jaworski

(57) ABSTRACT

A system to form and store an electrocardiogram (ECG) signal derived from a cardiac electrical signal that includes an apparatus having a pair of the electrodes to connect to a patient to detect the cardiac electrical signal. A signal sampler samples the cardiac electrical signal to form the ECG signal. A data storage device stores the ECG signal. A computer communicates with the data storage device to retrieve the ECG signal for analysis by software stored in the memory of the computer. The software analyzes a morphology of the amplitude of a plurality of R-wave peaks contained within the ECG signal and/or analyzes a morphology of the area of a plurality of QRS complex pulses contained within the ECG signal.

17 Claims, 10 Drawing Sheets

U.S. PATENT DOCUMENTS

| | | | |
|---|---|---|---|
| 5,105,354 | A | 4/1992 | Nishimura |
| 5,902,250 | A | 5/1999 | Verrier et al. |
| 6,415,174 | B1 * | 7/2002 | Bebehani et al. ............ 600/513 |
| 7,343,198 | B2 | 3/2008 | Bebehani |
| 2003/0055348 | A1 | 3/2003 | de Chazal et al. |
| 2006/0041201 | A1 | 2/2006 | Behbehani et al. |

OTHER PUBLICATIONS

Mendel, M., Chapeter 5, Uncertain Rule-Based Fuzzy Logic Systems: Introduction and New Directions, Prentice Hall, NF, 2001.

MIDMARK Diagnostics Group, article on Brentwood IQ mark EZ Holter Window System, found at www.midmarkdiagnostics.com, and www.discountcardiology.com/catalog/brentwood_iqmark_ezholter_windows_systems.

Benitez D., P.A. Gaydecki, A. Zaldi, and A.P. Fitzpatrick, The use of the Hilbert transform in ECG signal analysis. Computers in Biology and Medicine. 31:399-406, (2001).

de Chazal P., at al., Automated Processing of the Single-Lead Electrocardiogram for the Detection of Obstructive Sleep Apnoea, IEEE Transactions on Biomedical Engineering, Jun. 2003, vol. 50, No. 6, pp. 686-696.

de Chazal P., et al., Automatic Sleep Apnoea Detection using Measures of Amplitude and Heart Rate Variability from the Electrocardiogram, Pattern Recognition, 2002. Proceedings, 16th International Conference on, vol. 1, pp. 775-778 (2002).

Hanly P. et al., Increased Mortality Associated with Cheyne-Stokes Respiration in Patients With Congestive Heart Failure. Am. J. Respir. Crit. Care Med., vol. 153, No. 1, Jan. 1996; 272-276.

Khalil M. M. and A. Rifaie. Electrocardiographic changes in obstructive sleep apnoea syndrome. Respiratory Medicine. 92:25-27 (1998).

Moody G.B., at al., Clinical Validation of the ECG-Derived Respiration Technique, Computers in Cardiology; 1987; 4; p. 507-10.

Moody G.B., et al., Derivation of Respiratory Signals from Multi-Lead ECGs. Computers in Cardiology; 1985; 2; p. 113-6.

Penzel T., J. McNames, P. de Chazal, B. Raymond, A. Murray, and G. Moody. Systematic comparison of different algorithms for apnoea detection based on electrocardiogram recordings. Medical and Biological Engineering and Computing. 40:402-407, (2002).

Quaranta A.J., et al., Cheyne-Stokes Respiration During Sleep in Congestive Heart Failure, Chest 1997; 111-2; 467-473.

Roche F., et al., Cardiac Interbeat Interval Increment for the Identification of Obstructive Sleep Apnea, PACE, vol. 25, No. 8, pp. 1192-1199, Aug. 2002.

Travaglini A, et al., Respiratory Signal Derived from Eight-lead ECG's,, in Computers in Cardiology. Piscataway, NJ: IEEE Computer Society Press, 1998, vol. 25, pp.65-68.

Van Alste J.A., W. Van Eck, and O.E. Hermann, ECG baseline wander reduction using linear phase filterse, Computers and Biomedical Research. 19(5):417-427, (1986).

Young T., et al., Epidemiology of Obstructive Sleep Apnea. A Population Health Perspective. American Journal of Respiratory Critical Care Medicine, vol. 165. pp. 1217-1239, 2002.

Zywietz C., B. Widiger, and T. Penzel, Polysomnographic sleep recording with simultaneously acquired 12 lead ECGs: A study for detection and validation of apnea related ECG changes, Computers in Cardiology. 29:573-576, (2002).

U.S. Appl. No. 10/924,227, titled System, Software and Method for Detection of Sleep-Disordered Breathing Using an Electrocardiogram, allowed on Oct. 12, 2007.

File History of U.S. Appl. No. 10/924,227, Behbehani et al.

European Supplemental Search Report, issued in Application No. 05798754.7—1265, dated Sep. 25, 2009.

Mazzanti et al., "Validation of an ECG-derived respiration monitoring method," *Computers in Cardiology*, 30:613-616, 2003.

Redmond and Heneghan, "Electrocardiogram-based automatic sleep staging in sleep disordered breathing," *Computers in Cardiology*, 30:609-612, 2003.

Vijendra et al., "Frequency domain analysis of heart rate variability in sleep disordered breathing," *Proceedings of the 25th Annual International Conference of the IEEE EMBS*, Cancun, Mexico, pp. 208-211, Sep. 17-21, 2003.

European Office Action, issued in European Application No. 05798754.7-1265, mailed Jan. 19, 2010.

* cited by examiner

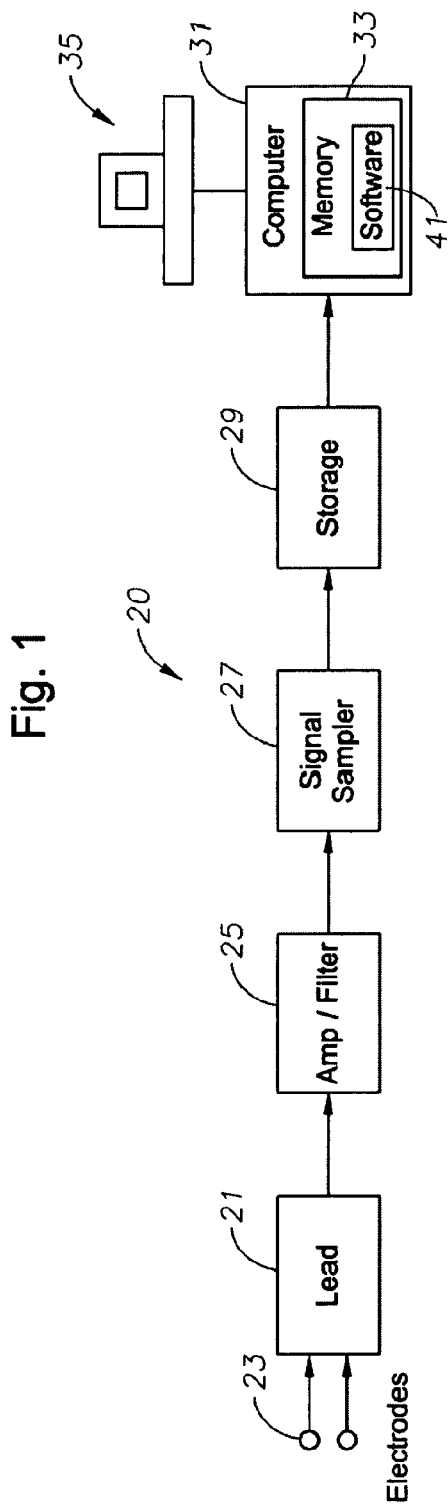
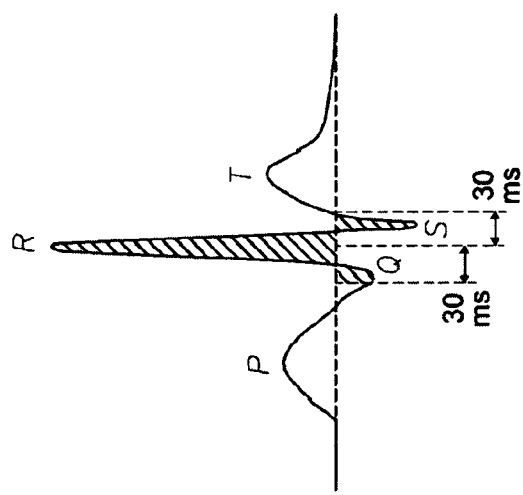

Time

Time (s)

Time (s)

SYSTEM, SOFTWARE, AND METHOD FOR DETECTION OF SLEEP-DISORDERED BREATHING USING AN ELECTROCARDIOGRAM

RELATED APPLICATIONS

This application is a continuation of and claims priority to and the benefit of U.S. patent application Ser. No. 10/924,227, titled "System, Software, and Method for Detection of Sleep-Disordered Breathing Using an Electrocardiogram," filed on Aug. 23, 2004, and issued on Mar. 11, 2008, as U.S. Pat. No. 7,343,198, incorporated herein by reference in their entirety.

BACKGROUND OF THE INVENTION

1. Field of the Invention

The present invention relates generally to diagnosis of sleep-disordered breathing and in particular to detection of sleep-disordered breathing events utilizing electrocardiographic measurements.

2. Description of the Related Art

Sleep-disordered breathing is a term applicable to a wide variety of sleep-related breathing disorders of diverse pathophysiologies that share the common characteristic of recurrent episodes of apnea and hypopnea during sleep. Sleep-disordered breathing has become a significant problem for a large portion of the population. In fact, sleep-disordered breathing has become prevalent in about 5% of the adult population and in almost 50% of patients with congestive heart failure.

Among the most common types of sleep-disordered breathing is sleep apnea, in which patients experience a complete cessation of air flowing into the lungs for periods exceeding ten seconds. Partial or complete arousal from sleep is considered a defensive mechanism most likely stimulated by rising carbon dioxide levels in the blood during the apneic event to reestablish ventilation and prevent death in the sleeping subject. There are three recognized types of sleep apnea: Central sleep apnea, Obstructive sleep apnea, and Cheyne-Stokes breathing. Central sleep apnea events are characterized by the suspension of all respiratory movement due to a decreased neural input from the brain to the muscles of inspiration. Obstructive sleep apnea is characterized by an upper airway occlusion. Cheyne-Stokes breathing is a waxing-waning pattern of breathing seen commonly in heart failure patients. The other form of sleep-disordered breathing, hypopnea, takes the form of a decrease in ventilation during sleep rather than a complete sleep apnea and is characterized by a reduction in the amplitude of breathing resulting in oxygen desaturation.

While the distinction between apnea and hypopnea is largely one of severity, sleep-disordered breathing diagnosis may entail measurement of both types of events. The Apnea-Hypopnea Index, representing a number of either apneic or hypopneic events per hour for a subject, is more commonly used than the Apnea Index, representing only the total number of apneic events per hour for the subject. An Apnea-Hypopnea Index of more than 5 events per hour, regardless of severity, is usually qualified as sleep apnea. Other variables such as average duration of an event, number of apneic versus hypopneic events, and average decrease in blood oxygen saturation during events are utilized to determine the severity of the disorder.

Polygraphic monitoring, or nocturnal polysomnography (the measurement of vital body signals during sleep) is the most commonly employed method of diagnosing sleep disorders, including sleep apnea. The overnight sleep study typically includes measurement of oronasal flow, thoracic and abdominal respiratory efforts, electrocardiogram (ECG), electroencephalogram (EEG), electrooculogram (EOG), chin and leg electromyogram (EMG), snoring sounds and pulse oximetry. The various signals are recorded during the night to identify different sleep stages, respiratory variables, heart function, and muscle tone, all of which aid in scoring sleep-disordered breathing events. The data from the measurements is collected during the patient's normal sleeping time and is later scored by a sleep specialist who visually examines the polygraph recording, identifying sleep stages and sleep-disordered breathing events causing oxygen desaturation. The sleep specialist's report contains a measure of sleep-disordered breathing known as the Apnea-Hypopnea Index (AHI), which refers to the number of irregular breathing events per hour of sleep.

Conventional polygraphic monitoring instrumentation is often very uncomfortable to the patient. For example, direct methods of respiration monitoring such as use of nasal thermistors, spirometers, and pneumotachometers, which measure air flow in and out of the lungs, generally interfere with normal respiration, and indirect methods, such as whole body plethysmographs, inductance and impedance plethysmographs, and strain gauge measurement of chest and abdomen circumference, which measure the effects of respiration on the body, either lose their calibration readily or immobilize the patient.

Polygraphic monitoring can have other significant disadvantages. For example, the cost of implementing polygraphic monitoring can exceed $1,500 per night making long-term studies cost prohibitive. Also, the methods of assessing long-term prognosis of sleep-disordered breathing require extensive patient cooperation. Further, sleep laboratories are inaccessible to a large part of the population due to limited facilities and long waiting lists. Home polysomnography, which allows the patient to conduct the test at home unattended, offers the patient a less expensive alternative, however, it has its own disadvantages including reduced accuracy.

Thus, there is a need for a system, software, and related methods that can detect events of sleep-disordered breathing that is simple to use, relatively inexpensive, noninvasive, and that requires only minimal patient cooperation.

Sleep-disordered breathing is prevalent in individuals suffering from cardiovascular disease. ECG signals are routinely recorded in studies for patients with cardiac problems, as well as in patients having respiratory disorders, sleep disorders, and patients in intensive care units. Millions of patients are screened each year using extended ECG monitoring (at least 24 hours), while generally their respiration is not monitored due to the added cost and inconvenience of conventional airflow monitoring equipment. Established technology has existed for years for measurement of the ECG in patients and advances in the field of electrocardiography have rendered analysis and conditioning of ECG signals robust. Measurement of ECG signals does not interfere with normal breathing and is more comfortable and less intrusive for the patient than polygraphic monitoring. Also, properly attached ECG leads are less prone to error due to patient movement. Correspondingly, use of the ECG to detect sleep-disordered breathing as an alternative to nocturnal polysomnography has been receiving increasing attention. Further, the ECG can provide cardiologists with simultaneous sleep-disordered breathing data and cardiac muscle activity data that may help improve diagnosis and treatment of associated cardiac disorders.

Investigators have examined various methodologies involving utilizing one or more parameters derived from the ECG to discriminate between normal breathing and breathing associated with sleep-disordered breathing. Generally, the focus is on deriving a waveform similar to respiration from the ECG. One methodology known as Heart Rate Variability identifies variations in the power spectrum of a time series of instantaneous heart rate calculated from the ECG. Another methodology known as Angle of Mean Electrical Axis also synonymously referred to as ECG-Derived Respiration (EDR) utilizes two orthogonal leads of the ECG to estimate an angle of the electrical axis. When used as the sole means of detecting sleep-disordered breathing, however, the detection results have been less than stellar. Proposed attempts to improve the reliability of this methodology in obtaining EDR include using 8 leads; however, no application of this multiple-lead methodology has been proposed for detecting sleep-disordered breathing.

More recently, an investigator has proposed a methodology deriving EDR from a single lead ECG combined with other parameters such as Heart Rate Variability to detect sleep apnea. EDR is first derived. The methodology then takes measurements using the power spectrum density of a timeseries of instantaneous heart rate, the power spectrum density of the EDR utilizing a sequence of R-wave areas, and a discrete sequence for one-minute time intervals, takes time domain ECG measurements from R-R intervals, and combines these measures to produce a diagnostic measure. Though proposed to use as little as one lead of the ECG, the methodology still requires use of instantaneous heart rate for the detection of sleep-disordered breathing.

Recognized by Applicant is that the morphology of the R-wave peak amplitudes on the QRS complex during obstructive sleep apnea episodes exhibited a variation which can negate the need for instantaneous heart rate for the detection of sleep-disordered breathing. Thus, it would be desirable to provide a system, software, and related methods to quantify the morphology of the QRS complex as a methodology of detecting sleep-disordered breathing, using either the morphology of the amplitude of the R-wave peaks in the ECG signal to detect the presence of sleep apnea or the morphology of the area under the QRS complex of the ECG signal, without requiring the use of instantaneous heart rate. It would also be desirable to provide such a system, software, and related methods that can detect events of sleep-disordered breathing utilizing ECG signal measurements, alone, that have high sensitivity and specificity.

SUMMARY OF THE INVENTION

In view of the foregoing, embodiments of the present invention advantageously provide a system, apparatus, and methods for detecting sleep-disordered breathing having a high sensitivity and specificity in identifying sleep-disordered breathing. Advantageously, embodiments of the present invention can detect events of sleep-disordered breathing using the electrocardiograph, alone, or as a supplement to other detection devices, to quantify the morphology of the QRS complex during obstructive sleep apnea episodes. Particularly, embodiments of the present invention provide a system, apparatus, and associated methods to quantify the morphology of the QRS complex as a methodology of detecting sleep-disordered breathing, using either the amplitude of the R-wave peaks in the electrocardiogram signal or the area under the QRS complex of the ECG, without requiring the use of instantaneous heart rate.

More specifically, embodiments of the present invention provide a system including an apparatus and software to form and store an electrocardiogram (ECG) signal from a cardiac electrical signal. The apparatus includes at least one ECG lead having at least one pair of the electrodes adapted to connect to a selected portion of a patient to detect the cardiac electrical signal. An amplifier/filter circuit is connected to the lead or leads to improve the cardiac signal. A signal sampler preferably in the form of an analog-to-digital converter having an appropriate sample rate, such as, for example, 250 hertz (Hz), is connected to the amplifier/filter circuit to sample the cardiac electrical signal to form the ECG signal. A data storage device, for storing the ECG signal, interfaces with the signal sampler. The system includes a computer positioned to communicate or interface with the data storage device to retrieve the ECG signal for analysis by software stored in the memory of the computer. The software is capable of analyzing a morphology of the amplitude of a plurality of R-waves contained within the ECG signal and/or capable of analyzing a morphology of the area of a plurality of QRS complex pulses. The software can include R-wave peak amplitude morphology analyzing software for analyzing a morphology of a plurality of R-waves contained within an ECG signal and QRS complex pulse area morphology analyzing software for analyzing a morphology of a plurality of QRS complex pulses in the ECG signal. The software is stored in the memory of the computer to form part of the system when in operation, but can also be independently stored and transported in a portable storage media.

The R-wave peak amplitude morphology analyzing software includes an R-wave peak amplitude determiner, which receives the ECG signal to determine a position and magnitude of the plurality of R-wave peaks within the ECG signal, variations in the magnitude of the plurality of R-wave peak amplitudes defining R-wave peak amplitude morphology for the plurality of R-wave peaks. The R-wave peak amplitude morphology analyzing software also includes an R-wave peak amplitude morphology analyzer. The R-wave peak amplitude morphology analyzer includes modules or components containing algorithms to form the R-wave peaks into a R-wave peak time series, determine the power spectral density for the R-wave peak time series, compare power levels of a predetermined frequency band within the power spectra to a predetermined threshold level value or values, and to signal detection of sleep-disordered breathing when a predetermined percentage of the power spectra indicates sleep-disordered breathing.

The QRS complex pulse area morphology analyzing software includes a QRS complex pulse area value determiner which utilizes the detected R-wave peak positions and amplitudes to determine a plurality of QRS complex pulse area values for at least portions of the ECG signal, each QRS complex pulse area value determined for a preselected time band less than 100 milliseconds wide and coincident with the position of corresponding R-wave peaks in the ECG signal. The QRS complex pulse area morphology analyzing software also includes a QRS complex pulse area value morphology analyzer, similar to the R-wave peak amplitude morphology analyzer. The QRS complex pulse area value morphology analyzer includes modules or components containing algorithms to form the QRS complex pulse area values into a QRS complex pulse area value time series, determine the power spectral density for the QRS complex pulse area value time series, compare power levels of a predetermined frequency band within the power spectra to a predetermined threshold level value or values, and to signal detection of sleep-disordered breathing when a predetermined percentage of the power spectra indicates sleep-disordered breathing.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

FIG. 1 is a schematic diagram of a system for detecting sleep-disordered breathing, according to an embodiment of the present invention.

FIG. 2 is a graph showing a portion of an electrocardiogram waveform.

DETAILED DESCRIPTION

Figure 3:
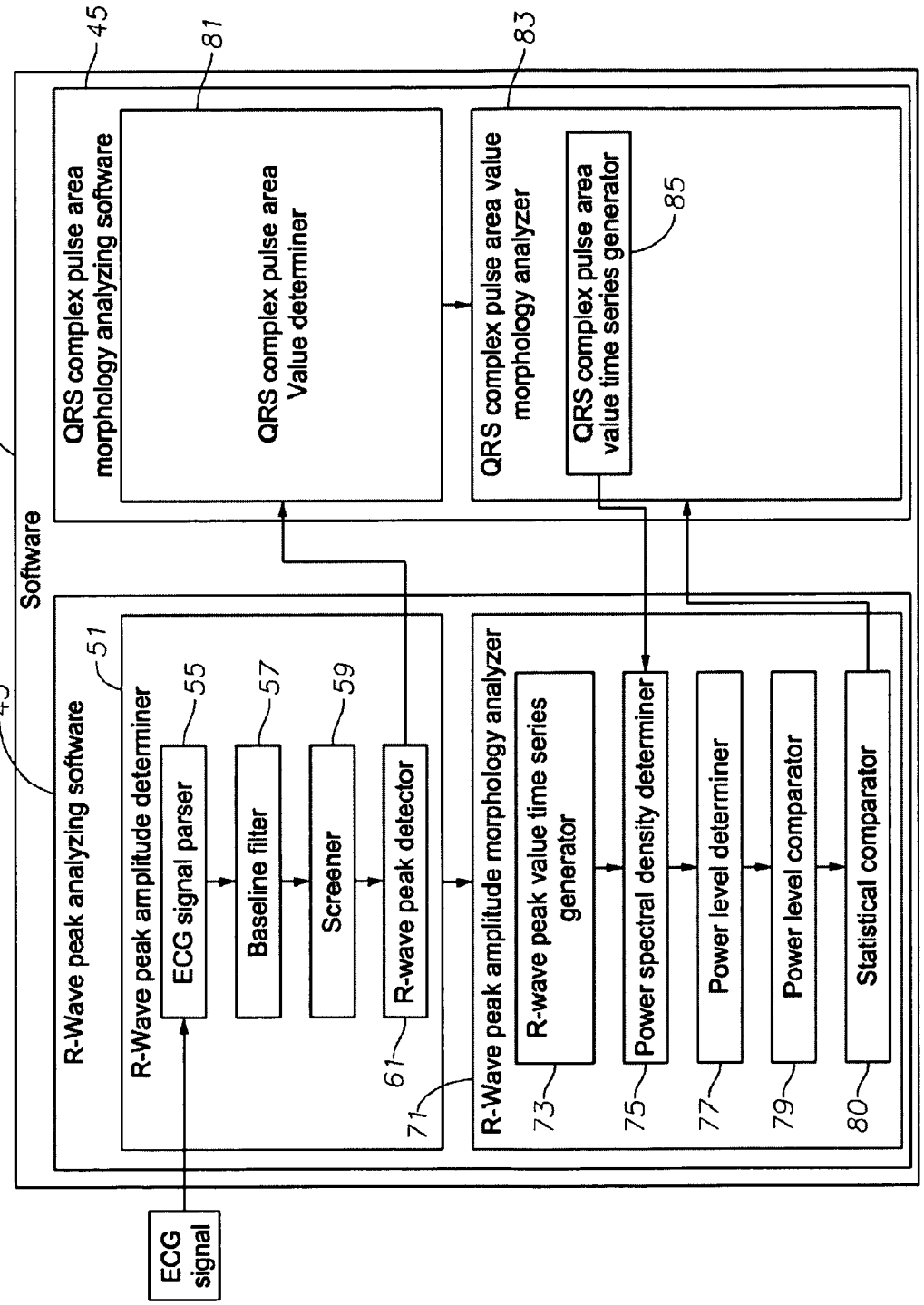
FIG. 3 is a schematic diagram of software to detect sleep-disordered breathing stored in the memory of a computer, according to an embodiment of the present invention.

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments. Note, the term "R-wave peak amplitude morphology" for a plurality of R-wave peaks refers to variations in the magnitude of a plurality of substantially consecutive R-wave peak amplitudes. The term "QRS complex pulse area morphology" for a plurality of QRS complex pulses refers to variations in at least a portion of the area for each of a plurality of QRS complex pulse associated with the plurality of substantially consecutive R-wave peak amplitudes.

Electrocardiography is based on the principle that current flow in the extracellular fluid is proportional to the rate of change of action potential in the myocardial cells of the heart. A plateau in the action potential produces a negligible current in the extracellular fluid, while repolarization and depolarization produce high currents. The mechanism of electrical conductivity in the body involves ionic currents (ions as charge carriers). Bi-potential body surface electrodes employed in electrocardiography transduce those ionic currents into electric currents, making it possible to record the bioelectric activity of the heart. Repolarization and depolarization in the myocardium may thus be seen as distinct events in the electrical signal transduced by these surface electrodes placed on the thorax. A recording of the electrical signal is referred to as an electrocardiogram. Various devices are known in the art, such as the Holter Monitoring System, made by Midmark Diagnostics Group of Torrance, Calif. that can record such electrocardiogram signals. Advantageously, embodiments of the present invention, particularly the system shown in FIG. 1, can incorporate such devices.

As perhaps best shown in FIG. 2, the ECG signals are conventionally characterized as including the P-, Q-, R-, and S-wave components. These components correspond to movement of the depolarization wave through the heart, causing contraction. The P-wave represents the electrical current in the atria (upper chambers of the heart). The QRS-waves (complexes) represent the electrical current traveling in the ventricles (lower chambers of the heart). The T-wave represents the electrical recovery period of the ventricles. Respiration affects ECG signals both through a low frequency baseline shift, which is routinely filtered as baseline noise, and by amplitude modulation of the QRS pulses, primarily due to chest movement, which changes the position of the leads relative to the heart. Sleep-disordered breathing can result in a change of the magnitude of the R-wave peaks and in the area of the QRS pulses.

As illustrated in FIGS. 1-15, embodiments of the present invention advantageously provide a system, software, and methods for detecting sleep-disordered breathing using an electrocardiogram (ECG) signal. More specifically, embodiments of the present invention provide a system including hardware and software, and related methods for detecting a position and magnitude of a plurality of R-wave peak amplitudes within an ECG signal, and analyzing the R-wave peak amplitude morphology from the ECG signal to detect sleep-disordered breathing. Further, embodiments of the present invention provide a system including hardware and software, and related methods for detecting a position of a plurality of QRS complex pulses within an ECG signal, determining a plurality of QRS complex pulse area values for a preselected time band, forming a QRS complex pulse area value of sampled time series, and analyzing the QRS complex pulse area morphology for the plurality of QRS complex pulses.

Referring to FIG. 1, a system according to an embodiment of the present invention generally includes an apparatus 20 to form and store an ECG signal from a cardiac electrical signal. The apparatus 20 includes at least one ECG lead 21 having at least one pair of the electrodes 23 adapted to connect to a selected portion of a patient to detect the cardiac electrical signal. An amplifier/filter circuit 25 is connected to the lead or leads 21 to improve the cardiac signal. A signal sampler 27, preferably in the form of an analog-to-digital converter having a suitable sample rate such as, for example, preferably 500 Hz or more preferably 1000 Hz, is connected to the amplifier/filter circuit 25 to sample the cardiac electrical signal to form the ECG signal. A data storage device 29 for storing the ECG signal, interfaces with the signal sampler 27. The data storage device 29 can take the form of a removable memory device, a storage unit in a remote computer adapted to communicate with the signal sampler 27 through a communication line, or a local computer positioned to communicate with the signal sampler 27 through an area network (not shown), just to name a few. The system includes a computer 31 having a memory 33 associated therewith positioned to communicate or interface with the data storage device 29 to retrieve the ECG signal for analysis and display on terminal 35 by software 41 stored in the memory 33 of the computer 31. The software 41 is capable of analyzing a morphology of a plurality of R-waves contained within the ECG signal and/or capable of analyzing a morphology of a plurality of QRS complex pulses in the ECG signal. Note, terminal 35 can be a simple monitor connected to computer 31 or can be a remote monitor/computer connected to the computer 31 through a network (not shown).

Referring to FIGS. 1 and 3, the following discussion related to software 41 generally refers to the preferred embodiment of the present invention which may include number values given for specific conditions and should not be construed as limitations. The software 41 includes R-wave peak amplitude morphology analyzing software 43 for analyzing a morphology of a plurality of R-waves contained within an ECG signal, and optionally includes QRS complex pulse area morphology analyzing software 45 for analyzing a morphology of a plurality of QRS complex pulses in the ECG signal. The software 41 is stored in memory 33 of computer 31 to form part of the system when in operation, but can also be independently stored on and transported in a storage media (not shown) such as, for example, a compact disc or digital videodisc, or other media known to those skilled in the art.

The R-wave peak amplitude morphology analyzing software 43 includes an R-wave peak amplitude determiner 51, adapted to receive the ECG signal or representation thereof, to determine a position and magnitude of the plurality of R-wave peaks (FIG. 2) within the ECG signal. Variations in the magnitude of the R-wave peak amplitudes define R-wave peak amplitude morphology for the R-wave peaks contained within the ECG signal. The R-wave peak amplitude determiner 51 can include functional modules or components, such as, an ECG signal parser 55. The ECG signal parser 55 is adapted to receive the ECG signal, to parse the ECG signal into a first plurality of epochs to improve accuracy by breaking the ECG signal down into manageable time segments, typically 900 seconds in length, which can be individually analyzed. Note, though the following software components can be implemented directly on the stored ECG signal, in the preferred embodiment of the present invention, there are significant advantages to dividing the ECG signal into a plurality of epochs for analysis. In an alternative methodology, however, the entire length of the ECG signal can be considered a single epoch and analyzed as such. Note also, the ECG signal parser 55, as with most of the other software modules or components, can be positioned functionally separate in memory of a remote computer (not shown) or in memory (not shown) associated with the apparatus 20.

The determiner 51 can also include a baseline filter 57, responsive to the ECG signal processor 55, to filter the epochs to substantially remove baseline wander, to thereby improve the accuracy of the analysis. The epoch baseline filter 57 preferably takes the form of a 200-point high-pass, linear-phase finite impulse response (FIR) filter with a cut-off frequency of 0.8 Hz, along with a bi-directional filter to null any group delay of the FIR filter. The determiner 51 can also include an epoch screener 59, responsive to the epoch baseline filter 57, to screen/eliminate any epoch displaying ECGs with either amplifier saturation (clipped R peaks), excessive movement artifact, noise bursts, large/excessive baseline wander, or high-frequency noise, to improve ultimate accuracy of the analysis. Occasionally, the sensed analog signals from ECG electrodes may saturate the amplifier used to amplify the signal. Amplifier saturation (clipped R-wave peaks) in the ECG signal can result in a flat R-wave peak time series (envelope). The number of samples of the ECG epoch that lie above predetermined limits of saturation specified is typically an indicator of amplifier saturation. Further, incessant baseline wander and large excursions in baseline may lead to ECG signal saturation not eliminated by the baseline filter 57. Excessive baseline wander retained in the ECG is identified by the algorithm by computing power of the filtered ECG signal in the lower frequency region (typically 0 to 1.0 Hz) of the power spectrum. In order to compare the low-frequency power against a preset threshold, the power computed over the 0 to 1.0 Hz frequency range is normalized by the total power in the spectrum. Epochs with a normalized value greater than, for example, 0.15 are discarded and ECGs with a normalized value less than the 0.15 are passed on to the next stage of screening.

Epochs with movement artifact and other noise bursts, and epochs with large amplitude high-frequency noise, may result in a large number of false positive R-wave peak identification. Thus, epoch screener 59 can screen/eliminate epochs containing transient noise bursts and powerline noise. Transient noise bursts are typically identified by deriving a measure of the variation in the power in the band 20 to 200 Hz of the power spectrum of the filtered ECG signal subdivided into a plurality of time segments. The power values obtained from the spectra of individual time segments sections of the ECG are normalized with respect to the total power in the respective spectra. A standard deviation of the power values of the time segments is then computed. If this measure exceeds a predetermined value, such as, for example 0.007, the algorithm should discard the epoch. Multiple harmonics of powerline noise are typically identified in the power spectrum of the filtered ECG signal in the frequency range of 180 to 200 Hz. A power value is computed for this range and normalized by the total power in the spectrum. If the normalized power value exceeds a predetermined threshold value, such as, for example 0.001, the algorithm should discard the epoch.

The determiner 51 can also include an R-wave peak detector 61, positioned to detect a plurality of R-wave peak positions and amplitudes values of the ECG signal within a selected plurality of epochs. The algorithm for the R-wave peak detector 61 can take many forms; however, in the preferred embodiment of the present invention, as partially illustrated in FIG. 7, the algorithm implements a Hilbert transform to conceptually form a template in order to locate the R-wave peaks (FIG. 10) within the ECG signal of the selected epochs, and a screen function to discard falsely detected R-wave peaks. The algorithm is discussed in further detail, later.

Figure 9:
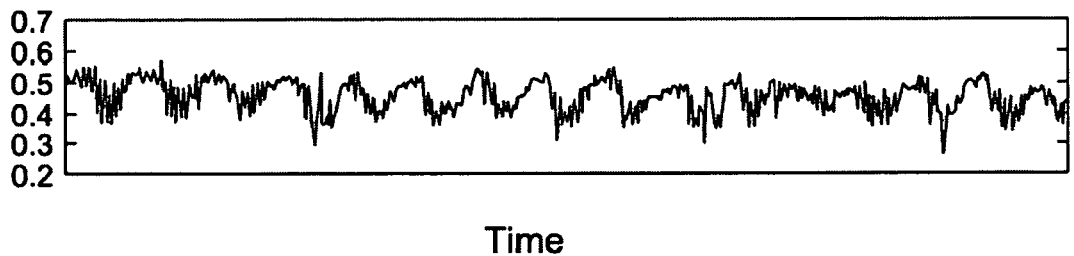
FIG. 9 is a graph showing an R-wave peak amplitude time series, according to an embodiment of the present invention.
Figure 11:
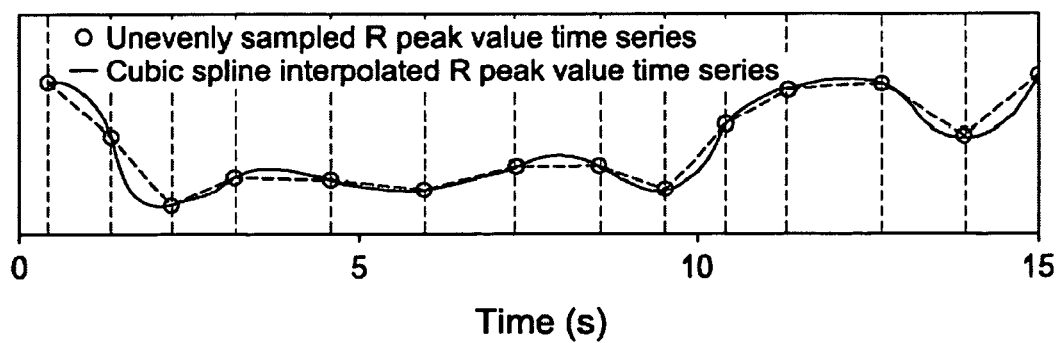
FIG. 11 is a graph showing an R-wave peak value trend formed by interpolating between the R-wave peak amplitudes depicted in FIG. 10.

Referring still to FIG. 3, the R-wave peak amplitude morphology analyzing software 43 further includes an R-wave peak amplitude morphology analyzer 71. The R-wave peak amplitude morphology analyzer 71 examines the determined R-wave peak amplitudes to detect or determine the existence of sleep-disordered breathing from variations in the magnitude of the plurality of R-wave peak amplitudes. These variations define R-wave peak amplitude morphology for the plurality of R-wave peaks in the selected epochs. The R-wave peak amplitude morphology analyzer 71 can include functional modules or components, such as, an R-wave peak value time series generator 73. The R-wave peak value time series generator 73 receives the R-wave peak amplitudes and positions from the R-wave peak amplitude determiner 51 and interpolates between consecutive R-wave peak amplitude values of the ECG signal separately for each selected epoch to form an R-wave peak value trend, as shown in FIG. 11. In the preferred embodiment of the present invention, this interpolation is implemented using a cubic spline algorithm, described later. The R-wave peak value time series generator 73 can then sample the R-wave peak value trend to further provide an evenly sampled R-wave peak value time series, as shown in FIG. 9.

Figure 12:
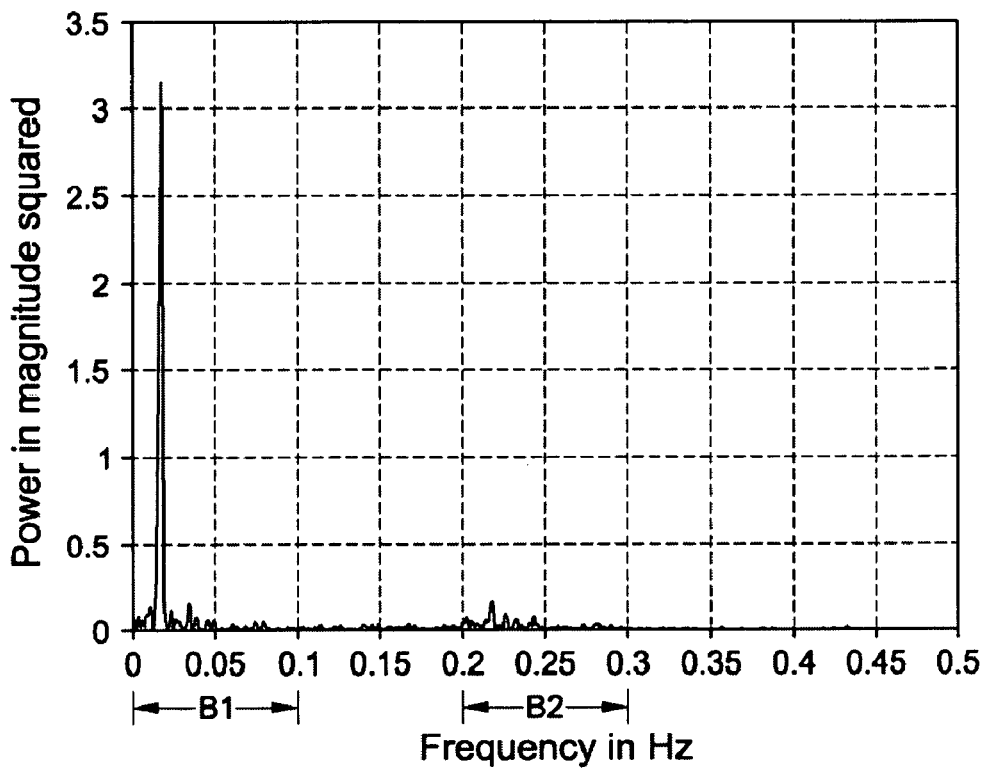
FIG. 12 is a graph showing power spectra of the R-wave peak amplitudes time series depicted in FIG. 9 for a patient having sleep-disordered breathing.
Figure 13:
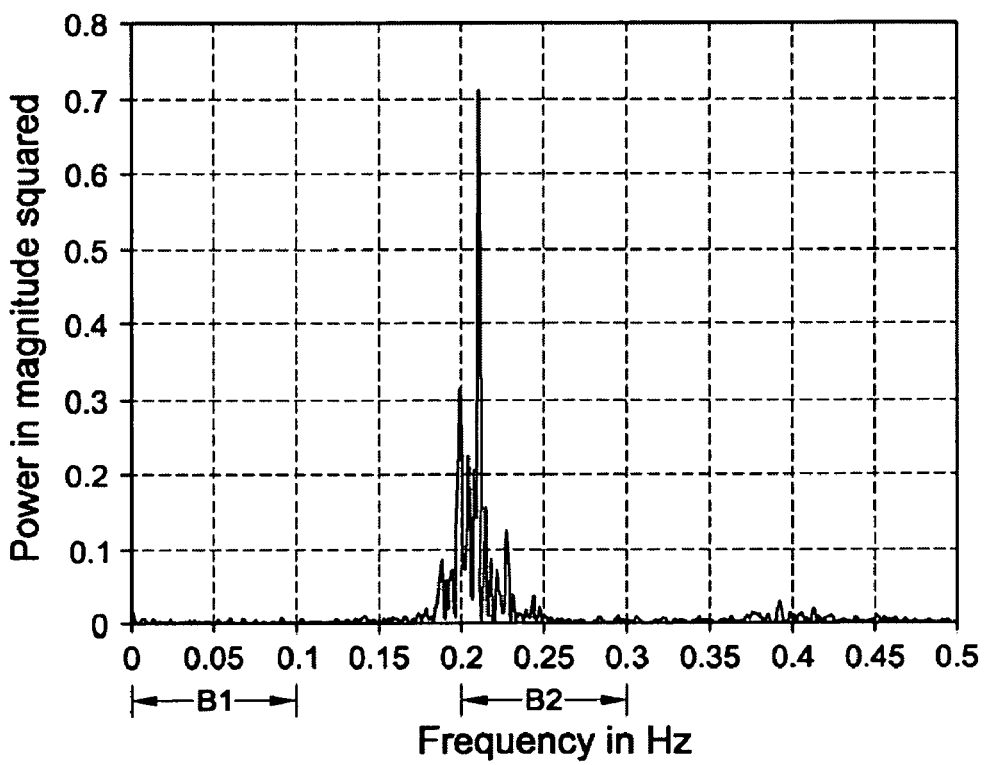
FIG. 13 is a graph showing power spectra of the R-wave peak amplitudes time series similar to that depicted in FIG. 9 for a patient not having sleep-disordered breathing.

A power spectral density determiner 75 determines the power spectral density for the newly formed R-wave peak value time series which should be detrended to remove any DC component to the R-wave peak value time series prior to conversion to the frequency domain. In the preferred embodiment of the present invention, power spectral density determiner 75 is implemented utilizing a Welch's averaged periodogram which is known and used in the art for estimating power spectral densities, and a Hanning window (function), also known and used in the art to further improve the frequency response of the resulting spectra. Generally, the Welch's averaged periodogram algorithm subdivides each epoch to be analyzed into a plurality of overlapping sections, determines the power spectral density for each section, and then averages the resultant power spectral density for each section to form a single power spectra for the epoch (FIGS. 12 and 13). The Hanning window is generally applied to the power spectral density for each section prior to averaging. Both the Welch's averaged periodogram and Hanning window are described in more detail, later.

A power level determiner 77 determines a power level value for a predetermined band or bands in the determined power spectral density. In the preferred embodiment of the present invention, the algorithm integrates the power spectral density function over the range determined by the predetermined band or bands to determine the power level in the predetermined band or bands. The bands can be varied through direct input from the user, but are preferably preset at 0 to 0.1 Hz and/or 0.2 to 0.3. These band power values can then be compared by a power level comparator 79 to a predetermined threshold power value, which can also be varied through direct input from the user, to determine whether or not the band power level value or values exceed the power threshold level value. Depending upon the band selected, if the band power level values exceeds or fails to meet a respective power threshold level value, the selected epoch is considered to contain sleep-disordered breathing events. Where multiple epochs rather than a single event or epoch is examined, statistical comparator 80 can compare the percentage of examined epochs containing sleep-disordered breathing events with a predetermined threshold percentage, selectable through direct input from the user. A probable existence of sleep-disordered breathing is determined and signaled if the percentage of examined epochs containing sleep-disordered breathing events exceed the predetermined threshold percentage.

Still referring to FIG. 3 and as stated above, software 41 also includes QRS complex pulse area morphology analyzing software 45 for analyzing a morphology of an area value for a plurality of QRS complex pulses in the ECG signal. The QRS complex pulse area morphology analyzing software 45 includes a QRS complex pulse area determiner 81 to determine the QRS complex pulse area values of the QRS complex pulses contained within each selected epoch. Each QRS complex pulse area is determined for a preselected time band less than 100 milliseconds wide but preferably 60 milliseconds wide (FIG. 2) and centered coincident with a position of corresponding R-wave peaks in the ECG signal. In the preferred configuration, the QRS complex pulse area determiner 81 implements the ECG signal parser 55 to form the plurality of epochs, the epoch baseline filter 57, the epoch screener 59, and the R-wave peak detector 61 to first detect the location of the R-wave peaks to thereby determine the QRS pulses area values.

Figure 14:
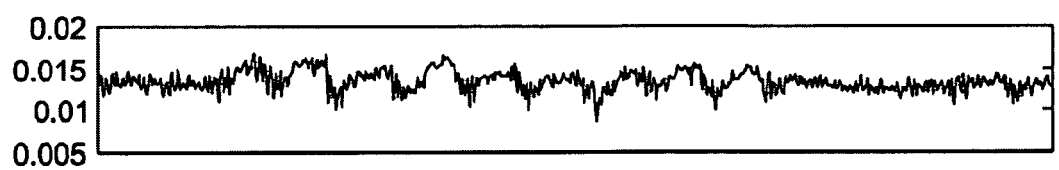
FIG. 14 is a graph showing a QRS complex pulse area value time series, according to an embodiment of the present invention.
Figure 15:
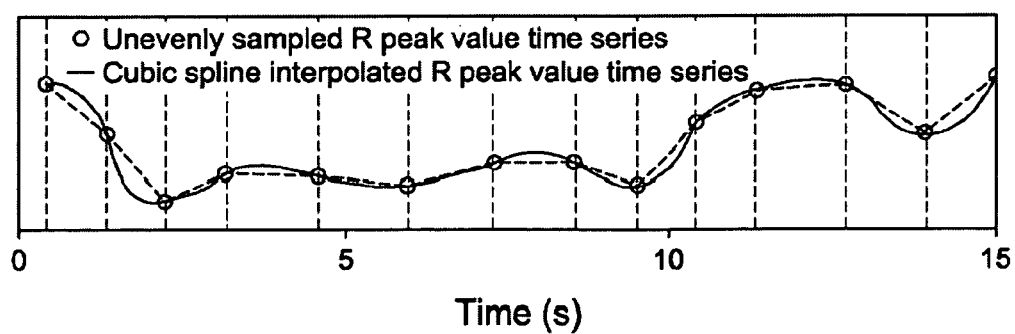
FIG. 15 is a graph showing a small time segment of a QRS complex pulse area value trend formed by interpolating between QRS complex pulse area values for the QRS complex pulse area value time series depicted in FIG. 14.

The QRS complex pulse area morphology analyzing software 45 further includes a QRS complex pulse area value morphology analyzer 83. The QRS complex pulse area value morphology analyzer 83 examines the determined QRS complex pulse area values to detect or determine the existence of sleep-disordered breathing from variations in the magnitude of the QRS complex pulse area values, which define QRS complex pulse area value morphology in the selected epochs. The QRS complex pulse area value morphology analyzer 83 includes a QRS complex pulse area value time series generator 85 which receives the QRS complex pulse area values from the QRS complex pulse area determiner 81 and interpolates between consecutive QRS complex pulse area values of the ECG signal separately for each selected epoch to form a QRS complex pulse area value trend, as shown in FIG. 15. The time series generator 85 is preferably implemented utilizing a cubic spline algorithm. The QRS complex pulse area value time series generator 85 can then sample the QRS pulses area value trend to further provide an evenly sampled QRS complex pulse area value time series, as shown in FIG. 14. The QRS complex pulse area morphology analyzing software 45 can then incorporate the power spectral density determiner 75, power level determiner 77, power level comparator 79, and the statistical comparator 80, with the input to the power spectral density determiner 75 being the QRS complex pulse area value time series rather than the R-wave peak value time series, as described above.

Figure 4:
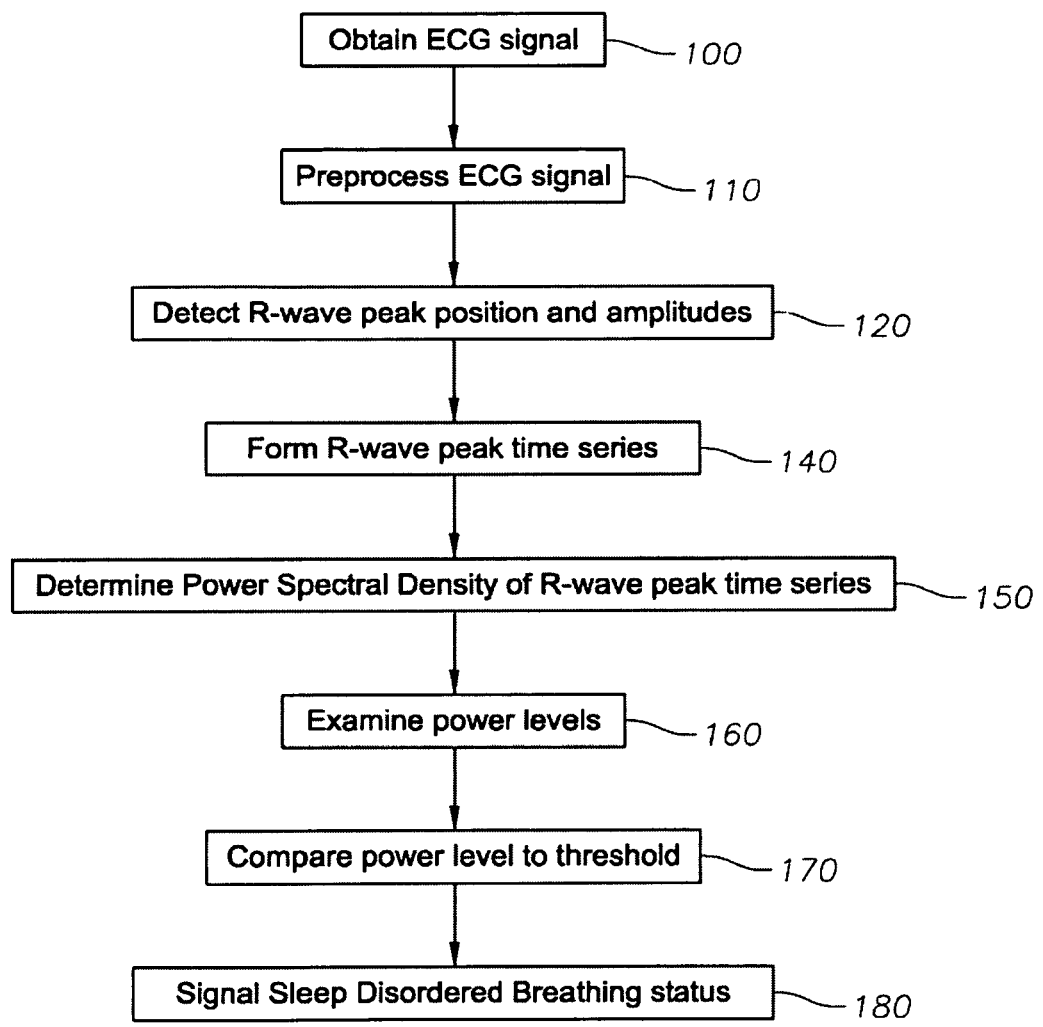
FIG. 4 is a schematic diagram of a high level flowchart depicting a method of detecting sleep-disordered breathing, according to an embodiment of the present invention.
Figure 5:
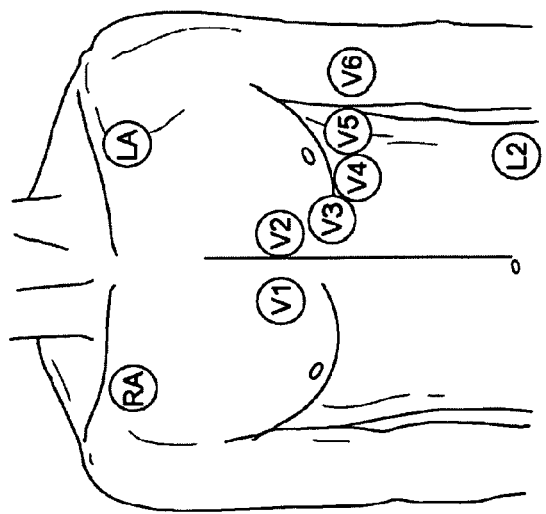
FIG. 5 is a partial perspective view of a patient showing standard electrocardiogram lead positions.

Embodiments of the present invention also include methods for detecting sleep-disordered breathing. Referring to FIG. 4, the ECG signal is first obtained (block 100) from a patient. ECG leads 21 via their associated electrodes 23 can be positioned in various standard or nonstandard locations upon the body of the patient. FIG. 5 shows standard lead positions currently used with various devices capable of monitoring cardiac electrical signals. Leads I and III have been found to provide the best overall signal; however, either of the remaining leads and various nonstandard lead positions (not shown) are within the scope of the present invention. Also referring to FIG. 1, generally, the cardiac electrical signal from the patient is amplified and filtered for various types of noises, known to those skilled in the art, by a circuit such as amplifier/filter circuit 25 to improve ECG signal quality. Amplifying and filtering can be accomplished both before and after sampling by the signal sampler 27. The sampling of the cardiac electrical signal results in the ECG signal. Sampling by signal sampler 27 is performed at a suitable rate, typically at least 100 Hz, but preferably 500 Hz, and more preferably 1000 Hz, but can be performed at a lower sampling rates and remain within the scope of the present invention. Obtaining the ECG signal can be performed at a medical facility or can be performed at a remote location, such as a patient's home. The data storage device 29 can take the form of a portable storage media such as a flash drive, portable hard disk, or a computer storage drive, or can be transmitted by telephone lines, wired and wireless communication means, cable, cellular, LAN, or other form of area network, to a local computer.

Figure 6:
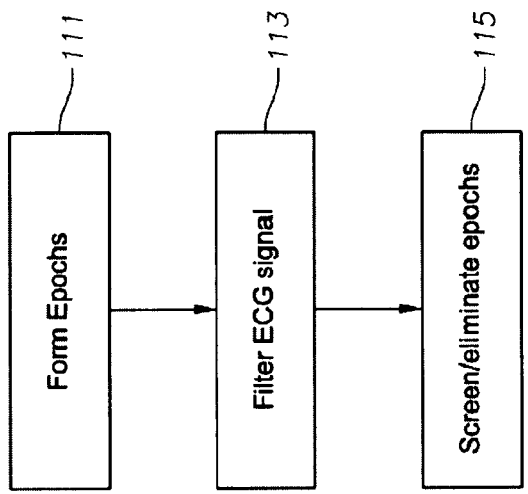
FIG. 6 is a schematic diagram of a flowchart depicting preprocessing of the electrocardiogram signal, according to an embodiment of the present invention.

Referring to FIGS. 4 and 6, the ECG signal is first preprocessed (block 110). Due to the investment in storage devices, such as data storage device 29, the ECG signal can be recorded for time frames exceeding eight hours. Thus, although an analysis can be performed on the entire ECG signal, in the preferred embodiment of the present invention, for analysis the ECG signal is divided into a plurality of epochs or clips (block 111) having a time block of, for example, 900 seconds. The 900 second time block generally provides an epoch having between 800 and 1200 R-wave peaks. This division of the ECG signal can be accomplished prior to storing or transmitting the ECG signal or upon retrieval or receipt of the ECG signal for analysis. Each epoch can be either simultaneously or sequentially examined. In the preferred embodiment of the present invention, however, each epoch is selected and examined sequentially and in a like manner. As such, most of the following discussion will focus on a single epoch.

To be able to analyze R-wave peak amplitude morphology or QRS complex pulse area morphology, a robust process is desired for accurately detecting the correct R-wave peak position and magnitude even under noisy conditions. The process of R-wave peak position detection in the present invention advantageously has a high accuracy of detection and low noise sensitivity, resulting in fewer false positives and fewer false negatives. The ECG signal is filtered (block 113) to remove low-frequency drift (known as baseline wander). Baseline wander generally results from movement of electrodes 23 caused by movement of the patient, including movement caused by respiration. In the preferred embodiment of the present invention, the filter (not shown) takes the form of a 200-point high-pass, linear-phase finite impulse response (FIR) filter with a cut-off frequency of 0.8 Hz, used to remove the baseline wander, along with bi-directional filtering, used to null any group delay of the FIR filter. Note, although filtering for baseline wander is preferably accomplished on each epoch, the filtering can be applied to the entire ECG signal prior to division. Note also, other linear and non-linear filtering means, including but not limited to other FIR filters having a different length, are within the scope of the present invention. Further, the filtering can be implemented either through software or through hardware.

Further, to improve accuracy, where the ECG signal is divided into a plurality of epochs, those epochs displaying ECG signals with amplifier saturation (clipped R peaks), excessive movement artifact, noise bursts, or large baseline wander, and those epochs with high-frequency noise can be screened/eliminated (block 115) from further analysis to improve ultimate accuracy of the analysis. The clipped R-wave peaks in the ECG signal can result in a flat R-wave peak time series (envelope). Further, incessant baseline wander and large excursions in baseline may lead to ECG signal saturation not eliminated by the filtering. Epochs with movement artifact and other noise bursts, and epochs with large amplitude high-frequency noise, may result in a large number of false positive R-wave peak detections.

Figure 7:
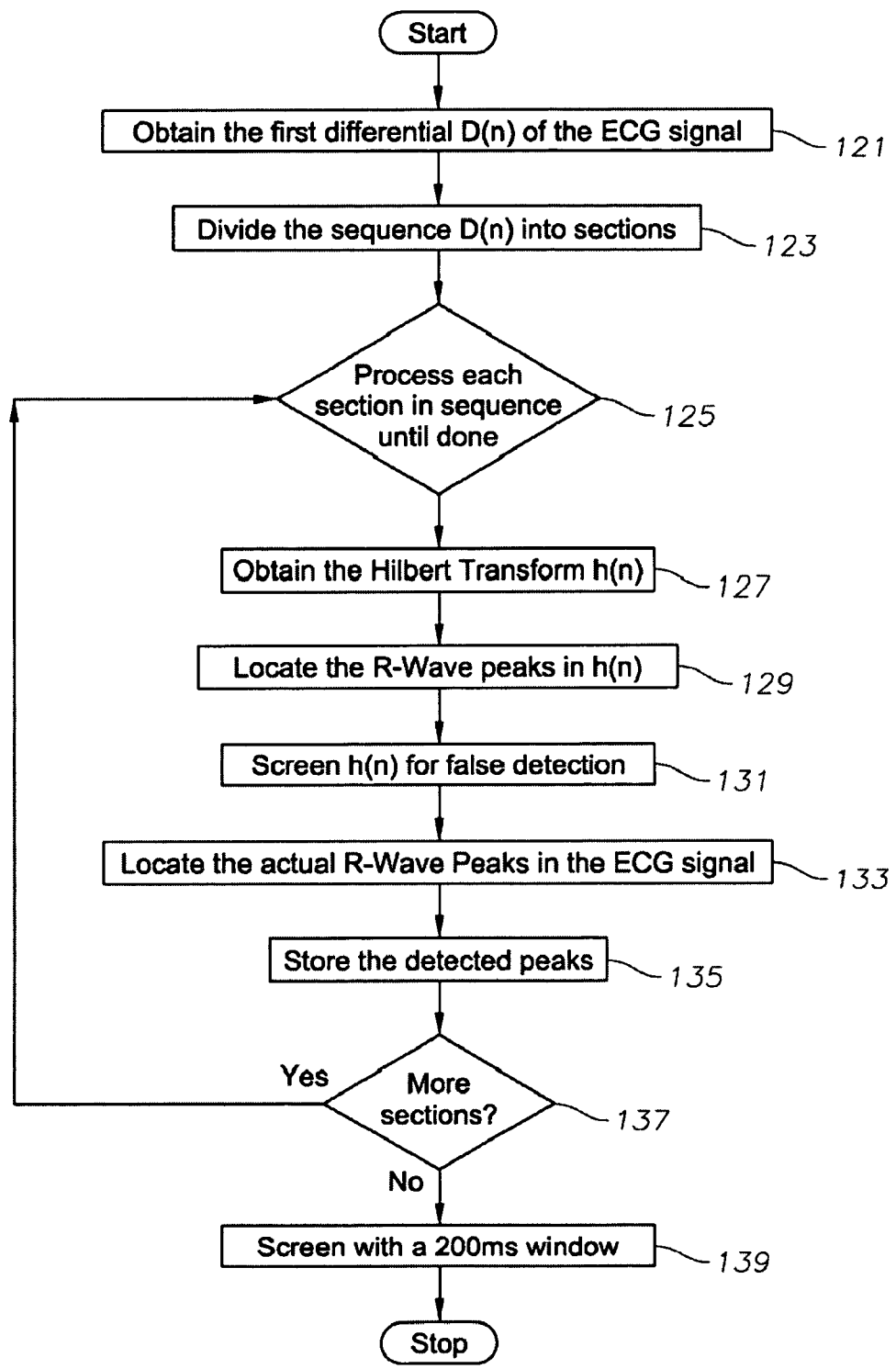
FIG. 7 is a schematic diagram of a flowchart depicting an R-wave peak detection algorithm, according to an embodiment of the present invention.
Figure 8:
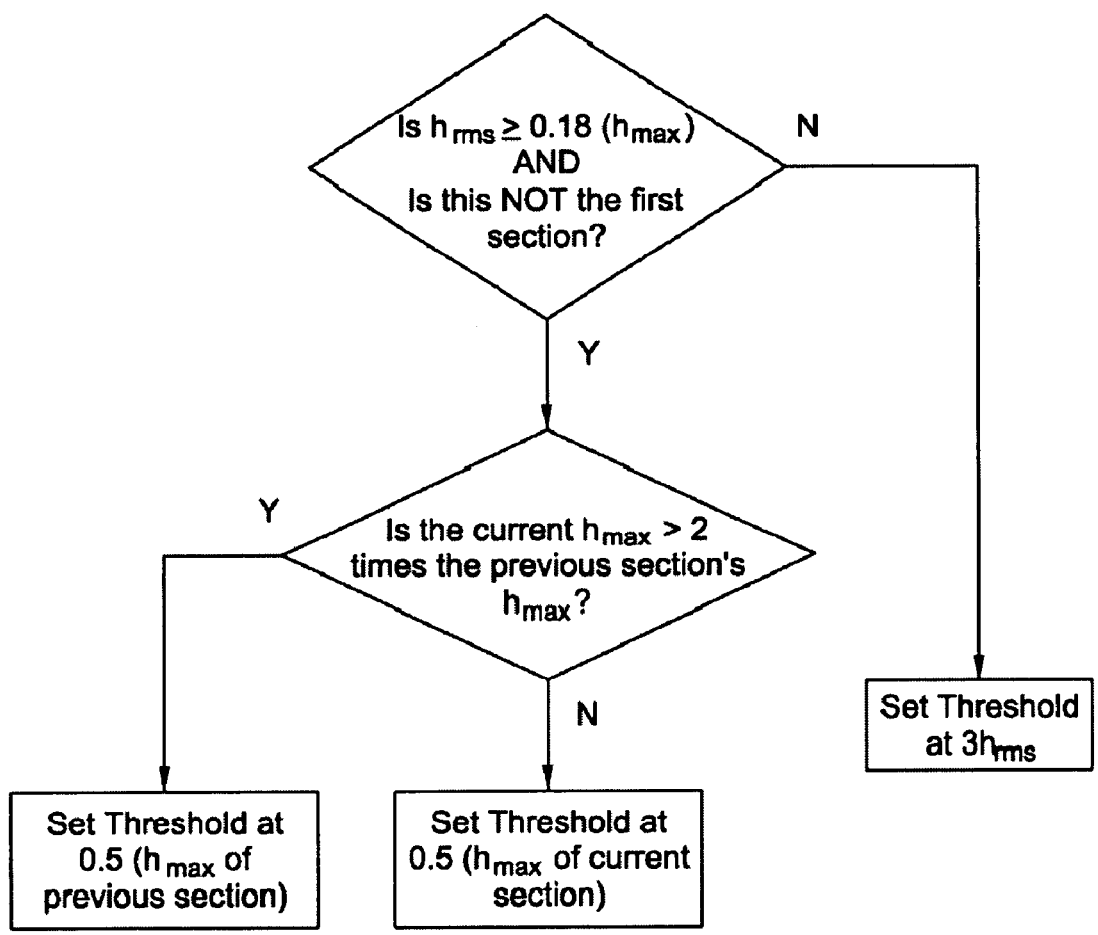
FIG. 8 is a schematic diagram of a flowchart depicting an adaptive threshold algorithm, according to an embodiment of the present invention.

Referring to FIGS. 4 and 7, R-wave peak positions and amplitudes are determined (block 120) from the ECG signal. There are a number of algorithms known to those skilled in the art capable of detecting the approximate location of a QRS complex, however, the selected methodology and algorithms described below are preferred. Referring primarily to FIG. 7, a first differential D(n) of the filtered ECG signal is obtained (block 121). The first differential is emulated by calculating:

$$D(n) = \frac{[x(n+1) - x(n-1)]}{(2T)}$$

for n=1, 2, ..., m−2, where, x represents the ECG signal, D represents the resulting differentiated signal, m is the total number of samples in the ECG signal (e.g., 900,000 for a 900 second epoch sampled at 1000 Hz), n is the sample number, and T is the sampling interval of the ECG signal; and where D(0)=D(1)/(2T), and D(m−1)=0. The differentiated signal D(n) is then divided into smaller sections (block 123), each of a preselected length. For example, for a sampling rate of 1000 Hz, and a length of five times the sampling rate, each section could be 5000 samples wide. Each section of the preselected length can then be selected sequentially (block 125) for further processing until each section is processed.

Next, for each of the sections of D(n), a transform such as, for example, a Hilbert transform h(n) is obtained (block 127) to create a "template" to locate the R-wave peaks in the ECG signal. First, a transform such as a Fast Fourier Transform (FFT) of the selected section is obtained. The DC component of the FFT sequence is then set to zero. The components of the FFT corresponding to the positive frequencies are multiplied by (−j) and those corresponding to the negative frequencies are multiplied by (j), where j represents the square root of negative one. An inverse FFT of the resulting sequence then gives the Hilbert transform of the original differentiated ECG signal for the selected section, where the real part of the above sequence is denoted h(n).

Next, the peaks in the Hilbert transform h(n) are determined (block 129). The peaks in the real part of the Hilbert transformed sequence h(n), represent regions of high probability of finding a true R-wave peak in a corresponding time frame of the ECG signal x(n). A threshold detector algorithm can be used to locate the peaks in the Hilbert transform sequence h(n). The algorithm can have an adaptive threshold such that the threshold value for each section is continually adjusted between sections. The adaptive threshold for each section can be determined as described below. First, the maximum value in h(n), hmax and the root mean square (RMS) value of the complete sequence h(n), hrms, is determined. The adaptive threshold value can then be determined according to the flowchart shown in FIG. 8. The peaks identified in the Hilbert transform sequence h(n) are then screened (block 131) for false detections. That is, if two peaks are located within, for example, 200 milliseconds of each other, the one with the lesser amplitude should be eliminated as a false detection.

Having now formed what can be described as a template for locating R-wave peaks, the screened Hilbert transform sequence h(n) is conceptually overlaid upon a corresponding period of the ECG signal to locate the actual R-wave peaks (block 133) in the corresponding period. Using the described algorithm, the corresponding R-wave peaks can be found within a few milliseconds of the detected peaks in the Hilbert transformed sequence h(n) in each section (search window). More specifically, the maximum value of the ECG signal within 50 milliseconds of each detected peak in h(n) is considered to be the detected R-wave peak. The detected R-wave peaks of the ECG signal corresponding to the current section are then stored (block 135). This process is continued for each successive section beginning at the last detected R-wave peak of the current section until each section is examined (block 137).

Having sequentially detected and accumulated a plurality of R-wave peaks, a final screening is performed (block 139). In this implementation, the algorithm assumes that only one R-wave peak can exist in a preselected time band or window, 200 milliseconds, for example. If more than one R-wave peak is found within the preselected time band, the R-wave peak with the greatest amplitude is considered to be the true R-wave peak and the other R-wave peaks, if so existing, are discarded.

Referring to FIGS. 4 and 9-11, having determined the R-wave peak positions and amplitudes from the ECG signal, an R-wave peak sampled (resampled) time series (FIG. 9) can be formed (block 140) by first interpolating between the detected consecutive R-wave peak amplitude values of the ECG signal (FIG. 10) to form an R-wave peak value trend (FIG. 11) and by sampling the formed R-wave peak value trend to thereby form any evenly sampled R-wave peak time series (FIG. 9). In the preferred embodiment of the present invention, cubic spline interpolation, a technique known in the art, can be used to generate the R-wave peak value trend. A cubic spline is a spline constructed of piecewise third-order polynomials which pass through a set of m data points. Cubic spline interpolation utilizes three consecutive original data points to calculate the coefficients in a cubic equation for a curve passing through those points. The resulting cubic equation is then employed to generate additional data points between the original data points. Thus, a series of cubic equations, each having (potentially) different coefficients, can be utilized to interpolate the R-wave peaks detected from the ECG signals described above. Though other algorithms are possible, cubic spline interpolation is preferred because a single polynomial cannot always interpolate all data points and can have a resulting curve that exceeds the range of the dataset. As illustrated in FIG. 11, the resulting R-wave peak value trend, however, can have unevenly spaced data points due to uneven spacing between the R-wave peak intervals. In order to improve the frequency response of the formed R-wave peak time series, the R-wave peak value trend can be resampled at, for example, 10 Hz to provide an R-wave peak time series having a uniform sample rate.

Referring to FIGS. 4, 12, and 13, having determined the R-wave peak sampled time series, the power spectral density of the R-wave peak sampled time series can be determined (block 150). In the preferred embodiment of the present invention, the R-wave peak sampled time series is first detrended by removing the mean. This functions to eliminate the DC component of the time series resulting in a spectrum that is more sensitive to frequency changes. The Welch's averaged periodogram method can then be used to determine the power spectral density of the R-wave peak sampled time series for a preselected frequency range. As identified previously, the Welch's averaged periodogram method is known and used in the art for estimating power spectral densities. It is generally carried out by dividing a time signal into successive blocks or sections and then averaging squared-magnitude discrete fourier transforms of signal blocks or sections. That is, using Welch's averaged periodogram method, for example, each epoch not screened or rejected can be subdivided to obtain overlapping spectra having less than the total number of sampled points. For example, for an epoch of 900 seconds sampled at 10 Hz, there would be 9000 samples. The Welch's averaged periodogram method can be utilized to obtain spectra with 1024 points in a preselected frequency range of approximately 0 to 0.5 Hz. This will provide between approximately 9-18 overlapping fast fourier transforms which are averaged to form one spectrum (FIG. 12) for the entire 900 second epoch.

A window function, such as the Hanning window (function) can also be used to further improve the estimation of the resulting spectra. The Hanning window is a tapering function used to bring another function, such as the R-wave time series, smoothly down to zero at the edges of the R-wave time series. The Hanning window functions to improve the accuracy of the fourier transform of the R-wave time series to enhance estimation of a spectrum of the R-wave peak value time series. This window can be applied directly to the power spectral density for each epoch or to each successive fourier transform performed on each block or section within the Welch's average periodogram.

Referring still to FIGS. 4, 12, and 13, a preselected band or bands B1, B2, of the resulting power spectral density is examined (block 160). Specifically, bands B1, B2, for the power spectra of a R-wave peak time series containing sleep-disordered breathing (FIG. 12) displays a statistically significant power level difference over that of the power spectra for a R-wave peak time series not containing sleep-disordered breathing (FIG. 13). In the preferred embodiment of the present invention, band B1 is approximately between the range of 0 to 0.1 and band B2 is approximately between the range of 0.2 to 0.3. Either one or both of the bands B1, B2, can be utilized in the following power level analysis, although analysis utilizing band B1 alone is preferred. The following description, however, will refer to both bands B1, B2.

Referring again to FIG. 4, a comparison (block 170) can then be made between at least one of the band power levels PB1, PB2, in the preselected frequency band or bands B1, B2, and a predetermined threshold level PTL obtained from statistical analysis of the power spectral for an average demographically similar patient not experiencing sleep-disordered breathing. The band power levels PB1, PB2, of the bands B1, B2, are obtained by integrating the power spectra obtained from the R-wave peak time series over the band frequency range, e.g., 0.0 to 0.1 HZ for PB1 and 0.2 to 0.3 HZ for PB2. The total power level TPL in, for example, the range 0 to 0.5 Hz, is computed and used to normalize the individual band power levels PB1, PB2, to give normalized band power levels NB1, NB2; e.g., NBx=PBx/TPL, where x=1 or 2. One or both of the normalized power levels NB1, NB2, are then compared to the predetermined threshold level PTLx. Depending on the implementation if the first normalized band power level NB1 exceeds the first predetermined threshold level PTL1, e.g. NB1>PTL1, or if the second normalized band power level NB2 fails to exceed the second predetermined threshold level PTL2, e.g. NB2<PTL2, the epoch is deemed to contain sleep-disordered breathing events.

Finally, where the percentage of epochs deemed to contain sleep-disordered breathing events, exceeds a predetermined percentage obtained from statistical analysis of average demographically similar patients not experiencing sleep-disordered breathing, the process signals (block 180) that sleep-disordered breathing has been detected in the patient. Note, in the preferred embodiment of the present invention, the predetermined threshold level PTLx is approximately 0.1 for band B1 and 0.5 for band B2, in normalized units, and the predetermined percentage is approximately 10%.

Figure 10:
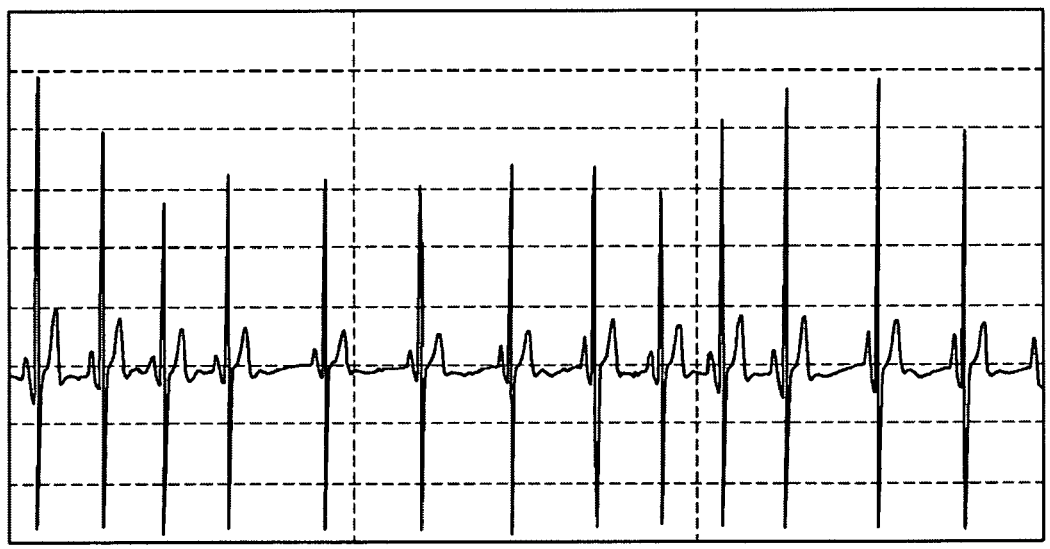
FIG. 10 is a graph showing detected R-wave peak amplitude values of the ECG signal, according to an embodiment of the present invention.

Referring to FIGS. 4 and 14-16, having determined the R-wave peak positions from the ECG signal (blocks 100-120), and thus, the location of a corresponding plurality of QRS complex pulses (FIG. 2) within the ECG signal, a QRS complex pulses area value sampled (resampled) time series (FIG. 14) can be formed (block 240) and analyzed (FIG. 16) as an alternate methodology for detecting sleep-disordered breathing. Individual QRS complex pulse area values coinciding with each determined R-wave peak in the ECG signal can be determined by rectifying and integrating the ECG signal over an interval spanning less than 50 milliseconds but preferably 30 milliseconds left and right of the respective R-wave peak position (FIG. 10). The computed QRS complex pulse area values for data points. The QRS complex pulse area value sampled time series (FIG. 14) is then formed by interpolating between the computed QRS complex pulse area values of the ECG signal to form a QRS complex pulse area value trend (FIG. 15) and by sampling the formed QRS pulse area value trend to thereby form an evenly sampled QRS complex pulse area value sampled time series (FIG. 14). As with the formation of the R-wave peak value trend, the preferred methodology of forming the QRS complex pulse area value trend includes use of cubic spline interpolation. This trend is then preferably sampled at 10 Hz to provide an evenly sampled QRS complex pulse area value sampled time series (FIG. 14).

Figure 16:
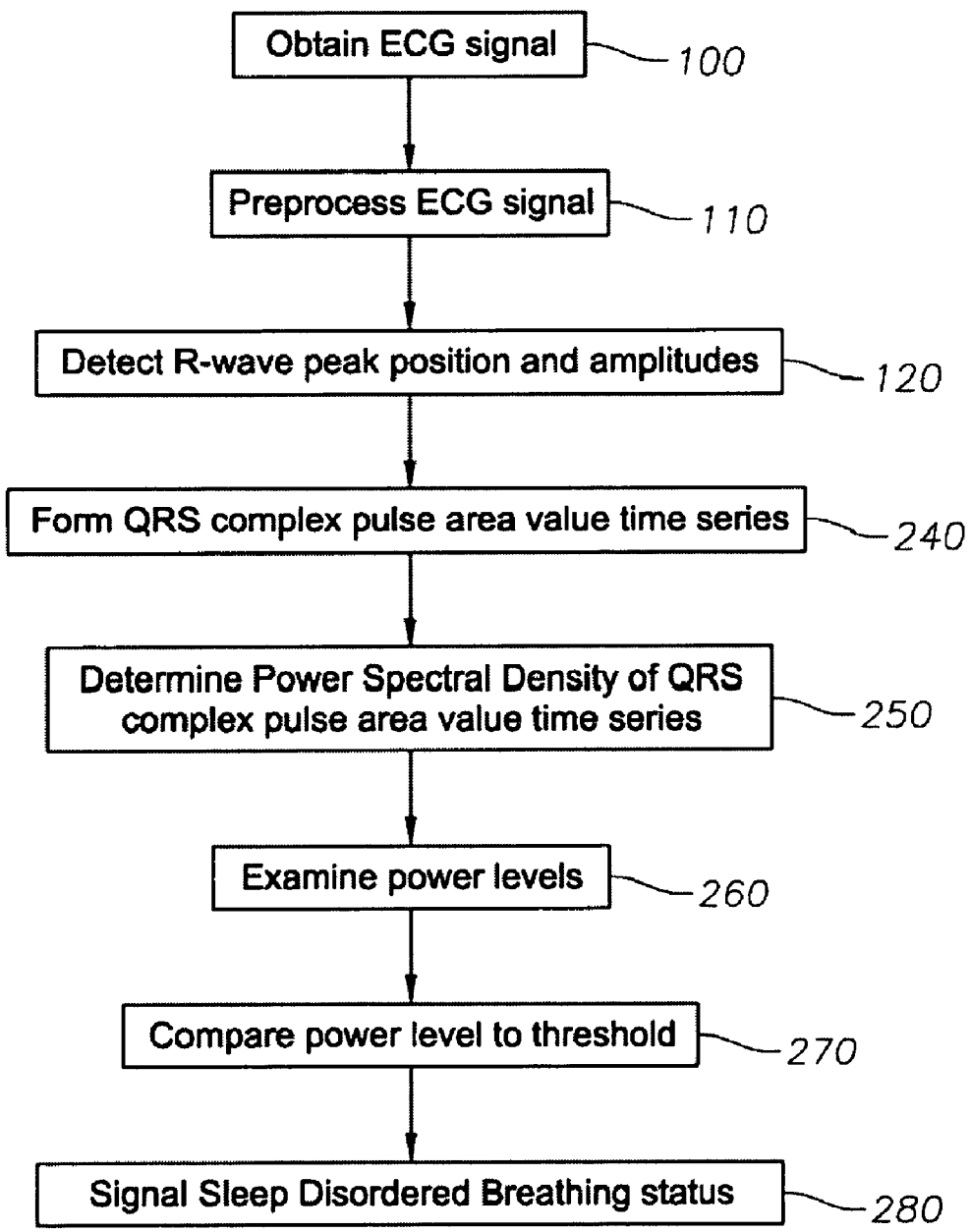
FIG. 16 is a schematic diagram of a high level flowchart depicting a method of detecting sleep-disordered breathing, according to an embodiment of the present invention.

Referring still to FIG. 16, the remaining steps 250-280 generally coincide with steps 150-180 and the algorithms used therewith. That is, the power spectral density of the QRS complex pulse area value sampled time series can be determined (block 250) using a method, such as, the Welch's average periodogram method, as described above. Further, preselected bands of the resulting power spectral density coinciding with bands B1, B2, are examined (block 260) to determine their respective power levels. As described with respect to the R-wave peak sampled time series, a comparison can then be then made (block 270) between at least one of the band power levels and a corresponding predetermined threshold level. The comparison can be made using raw or normalized band power level values. If either or both of the predetermined threshold levels are either exceeded or not met, depending upon which band is examined, the epoch is deemed to contain sleep-disordered breathing events. Where multiple epochs are examined, if the percentage of epochs deemed to contain sleep-disordered breathing events, exceeds a predetermined percentage, the process signals (block 280) that sleep-disordered breathing has been detected in the patient. Note, as described with respect to the analysis of the R-wave peak time series, the predetermined threshold level PTLx is approximately 0.1 for band B1 and 0.5 for band B2, in normalized units, and the predetermined percentage is approximately 10%.

The invention has significant advantages. Embodiments of the present invention can be applied in various forms and in various patient diagnostic settings. For example, embodiments of the present invention can be utilized with 24-hour ECG recordings commonly obtained from persons suspected of having cardiac disorders to determine if the disorders are exacerbated by sleep-disordered breathing. Also, for example, embodiments of the present invention can be used as a screening tool with patients suspected of having sleep-disordered breathing, either prior to going through a more expensive polysomnography or as a potential substitute. Further, embodiments of the present invention can be used as part of a bedside monitor for detection of sleep-disordered breathing, in not only hospitalized or critically ill patients, but as part of a home monitoring system. Embodiments of the present invention can potentially be used to replace expensive and not readily available polysomnography (overnight sleep studies) to diagnose sleep-disordered breathing, and can obviate the need for flow or pressure sensing devices for detection of sleep apnea that are often complicated to use with patients during sleep. A major advantage of embodiments of the present invention is its simplicity of use and ability in making long-term studies feasible. Embodiments of the present invention can be utilized by cardiologists, pulmonologists, or general practitioners to assist them in diagnosing patients with sleep-disordered breathing, military doctors monitoring personnel operating critical devices for sleep-disordered breathing, and manufacturers of bedside cardiac monitors, polysomnography systems, Holter monitors, etc., to improve the diagnostic accuracy of such devices.

This application is related to U.S. patent application Ser. No. 10/924,227, titled "System, Software, and Method for Detection of Sleep-Disordered Breathing Using an Electrocardiogram," filed on Aug. 23, 2004, and issued on Mar. 11, 2008, as U.S. Pat. No. 7,343,198, incorporated herein by reference in their entirety.

While the invention has been shown in only two of its forms, it should be apparent to those skilled in the art that is it not so limited, but is susceptible to various changes, without departing from the scope of the invention. For example, although the foregoing description focused on implementation for use of software, much of the methodology can instead be implemented through use of hardware. Further, although the foregoing description focused on frequency-domain based methods for the analysis of the R-wave peak amplitude of the ECG signal, time-domain methods such as computation of standard deviation of the R-wave time series can be combined with the frequency-domain parameters to improve performance. Such time-domain methods could also help detect hypopneas with a higher sensitivity and specificity. In addition, established methods based on heart rate variability can be incorporated to further increase the detection performance. A detector based on fuzzy-logic or a pattern recognition system can also be used to supplement the threshold method presented here. Also for example, rather than storing the ECG signal for the entire monitored time period, the ECG signal can be stored in the form of a plurality of epochs of a preselected size. The ECG signal can be filtered as part of the storing process rather than the during R-wave peak detection process. Prior to storing, epochs composed of filtered ECG signal can be screened and rejected for failure to meet described criteria. This would minimize storage requirements and/or data transmission requirements. Further, the system could be automated to provide an "SDB Index" based on the power values derived from the complete night's data similar to the diagnosis provided using the AHI. Still further, although specific values and percentages were supplied, these values and percentages only apply to the preferred embodiment of the present invention. Different values and percentages can be utilized depending upon the desired statistical accuracy.

That claimed is:

1. A method for detecting sleep-disordered breathing, the method comprising:
   detecting a plurality of QRS complex pulses within an electrocardiogram signal from only a single lead;
   determining a plurality of QRS complex pulse area values for a preselected time band, variations in the area of each of the plurality of QRS complex pulse areas defining QRS complex pulse area morphology for the plurality of QRS complex pulses;

analyzing the QRS complex pulse area morphology for the plurality of QRS complex pulses; and detecting sleep disordered breathing, when existing, responsive to the analysis of the change in value between the area of each of the plurality of QRS complex pulse areas.

2. A method as defined in claim 1, further comprising the step of:

forming a QRS complex pulse area value sampled series by interpolating between QRS complex pulse area values of an electrocardiogram signal to form a QRS complex pulse area value trend and by sampling the formed QRS complex pulse area value trend; and wherein the step of analyzing the QRS complex pulse area morphology of the plurality of QRS complex pulses includes the steps of:

determining a power spectral density of the QRS complex pulse area value sampled series, and determining a power level in a preselected frequency band of the power spectral density.

3. A method as defined in claim 2, further comprising the step of comparing the determined power level to a predetermined threshold level to determine if the predetermined threshold level is exceeded.

4. A method as defined in claim 2, wherein the preselected frequency band is a first frequency band having a first power level, the method further comprising performing at least one of the following steps:

comparing the first power level to a first predetermined threshold level to determine if the first predetermined threshold level is exceeded, the preselected frequency band approximately between 0.0 to 0.1 Hz; and comparing a second power level of a second frequency band to a second predetermined threshold level to determine if the second power level fails to exceed the second predetermined threshold level, the second preselected frequency band approximately between 0.2 to 0.3 Hz.

5. A method as defined in claim 2, wherein the preselected time band is less than 100 milliseconds wide.

6. A method as defined in claim 1, further comprising the steps of:

dividing the electrocardiogram signal into a first plurality of epochs;

forming an QRS complex pulse area value sampled series for each epoch in a subset of the first plurality of epochs defining a second plurality of epochs by interpolating between QRS complex pulse area values of each epoch in the second plurality of epochs to form an QRS complex pulse area value trend for each epoch in the second plurality of epochs and by sampling the formed QRS complex pulse area value trend for each of the second plurality of epochs; and determining a power spectral density of the QRS complex pulse area value sampled series for each of the second plurality of epochs.

7. A method as defined in claim 6, further comprising the steps of:

determining a power level in a preselected frequency band of the power spectral density for each of the second plurality of epochs;

comparing the determined power level for each of the second plurality of epochs to a predetermined threshold level to determine if the predetermined threshold level is exceeded; and determining the existence of sleep-disordered breathing when a preselected percentage of second plurality of epochs exceed the predetermined threshold level.

8. A method as defined in claim 1, further comprising the steps of:

determining a power level in a preselected frequency band of the power spectral density for each of a plurality of epochs;

comparing the determined power level for each of the plurality of epochs to a predetermined threshold level to determine if the predetermined threshold level is exceeded; and determining the existence of sleep-disordered breathing when a preselected percentage of the plurality of epochs fails to exceed the predetermined threshold level.

9. A non-transitory computer readable medium that is readable by a computer facilitating detecting sleep disordered breathing in a patient, the computer readable medium comprising a set of instructions that, when executed by the computer, cause the computer to perform the following operations:

detecting a plurality of QRS complex pulses within an electrocardiogram signal from only a single lead;

determining a plurality of QRS complex pulse area values for a corresponding plurality of QRS complex pulses within an electrocardiogram signal, variations in the area of each of the plurality of QRS complex pulse areas defining QRS complex pulse area morphology for the plurality of QRS complex pulses;

analyzing the change in value between the area of each of the plurality of QRS complex pulse areas; and detecting sleep disordered breathing, when existing, responsive to the analysis of the change in value between the area of each of the plurality of QRS complex pulse areas.

10. A non-transitory computer readable medium as defined in claim 9, wherein the operations further comprise forming a QRS complex pulse area value sampled series by interpolating between QRS complex pulse area values of an electrocardiogram signal to form a QRS complex pulse area value trend and by sampling the formed QRS complex pulse area value trend; and wherein the operation of analyzing the change in value between the area of each of the plurality of QRS complex pulse areas includes the operations of:

determining a power spectral density of the QRS complex pulse area value sampled series, and determining a power level in a preselected frequency band of the power spectral density.

11. A non-transitory computer readable medium as defined in claim 10, wherein the operations further comprise comparing the determined power level to a predetermined threshold level to determine if the predetermined threshold level is exceeded.

12. A non-transitory computer readable medium as defined in claim 10, wherein the operations further comprise comparing a power level the preselected frequency band to a predetermined threshold level to determine if the predetermined threshold level is exceeded, the preselected frequency band approximately between 0.0 to 0.1 Hz.

13. A non-transitory computer readable medium as defined in claim 10, wherein the operations further comprise comparing a power level of the preselected band to a predetermined threshold level to determine if the power level fails to exceed the predetermined threshold level, the preselected frequency band approximately between 0.2 to 0.3 Hz.

14. A non-transitory computer readable medium as defined in claim 10, wherein the preselected time band is less than 100 milliseconds wide.

15. A non-transitory computer readable medium as defined in claim 10, wherein the operation of determining a power level in a preselected frequency band of the power spectral density comprises determining a power level in a preselected frequency band of the power spectral density for each of a plurality of epochs, and where in the operations further comprise:
- comparing the determined power level for each of the plurality of epochs to a predetermined threshold level to determine if the predetermined threshold level is exceeded; and
- determining the existence of sleep-disordered breathing when a preselected percentage of the plurality of epochs fails to exceed the predetermined threshold level.

16. A non-transitory computer readable medium as defined in claim 9, wherein the operations further comprise:
- dividing the electrocardiogram signal into a first plurality of epochs;
- forming an QRS complex pulse area value sampled series for each epoch in a subset of the first plurality of epochs defining a second plurality of epochs by interpolating between QRS complex pulse area values of each epoch in the second plurality of epochs to form an QRS complex pulse area value trend for each epoch in the second plurality of epochs and by sampling the formed QRS complex pulse area value trend for each of the second plurality of epochs; and
- determining a power spectral density of the QRS complex pulse area value sampled series for each of the second plurality of epochs.

17. A non-transitory computer readable medium as defined in claim 16, wherein the operations further comprise:
- determining a power level in a preselected frequency band of the power spectral density for each of the second plurality of epochs;
- comparing the determined power level for each of the second plurality of epochs to a predetermined threshold level to determine if the predetermined threshold level is exceeded; and
- determining the existence of sleep-disordered breathing when a preselected percentage of second plurality of epochs exceed the predetermined threshold level.

* * * * *